(12) United States Patent
Hagedorn et al.

(10) Patent No.: US 6,177,126 B1
(45) Date of Patent: *Jan. 23, 2001

(54) PROCESS FOR THE PRODUCTION OF A MATERIAL FOR SEALING AND HEALING WOUNDS

(75) Inventors: Olaf Hagedorn, Warendorf; Ulrich Schiele, Ottobrunn, both of (DE)

(73) Assignee: Nycomed Arzneimittel GmbH, Ismaning bei Munchen (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/934,748

(22) Filed: Sep. 22, 1997

Related U.S. Application Data

(63) Continuation-in-part of application No. 08/437,232, filed on May 8, 1995, which is a continuation-in-part of application No. 08/220,877, filed on Mar. 31, 1994, now abandoned.

(30) Foreign Application Priority Data

Mar. 31, 1993 (AT) ........................................ 647/93

(51) Int. Cl.⁷ .............................. B05D 1/26; B05D 1/34; B05D 7/04; B67D 3/00

(52) U.S. Cl. ........................ 427/2.31; 118/25; 118/325; 118/612; 222/486; 427/2.12; 427/2.13; 427/394; 427/420; 604/368

(58) Field of Search ..................... 427/2.1, 2.31, 427/394, 420, 2.12, 2.13, 2.14; 118/25, 325, 612, 693; 222/485, 486; 604/304, 368

(56) References Cited

U.S. PATENT DOCUMENTS

| 1,036,108 | 8/1912 | Harton . | |
|---|---|---|---|
| 1,137,683 | 4/1915 | White | 222/486 |
| 1,390,383 | 9/1921 | Powell . | |
| 1,546,411 | 7/1925 | Short | 222/486 |
| 2,821,958 | 2/1958 | Litty . | |
| 3,505,963 | 4/1970 | Westling . | |
| 3,965,860 | 6/1976 | Cone et al. | 118/612 |
| 4,453,939 | 6/1984 | Zimmerman et al. | 604/368 |

(List continued on next page.)

FOREIGN PATENT DOCUMENTS

| 616353 | 1/1936 | (DE) . |
|---|---|---|
| 693 222 | 6/1940 | (DE) . |
| 201330 | 12/1958 | (DE) . |
| 23 41 091 | 2/1975 | (DE) . |
| 40 00 405 | 7/1991 | (DE) . |
| 0 472 050 | 2/1992 | (EP) . |

OTHER PUBLICATIONS

P.R. Schulz, "Ejection Soldering", IDM Technical Disclosure Bulletin, Vo. 5, No. 1 (Jun. 1962), p. 7.

Primary Examiner—Diana Dudash
(74) Attorney, Agent, or Firm—Wenderoth, Lind & Ponack, L.L.P.

(57) ABSTRACT

A process for producing a material for sealing and/or healing wounds fills a liquid composition into a container having two or more plates. At least two of the plates are perforated with one or more flow-through holes. At least one of the perforated plates is movable relative to another of the perforated plates. A suitable carrier is transported below the container in transport direction. The perforated plates are then continuously moved relative to each other so as to allow the liquid composition to drip onto the carrier being transported below the container. The liquid composition can thus be substantially evenly applied to the carrier.

76 Claims, 7 Drawing Sheets

U.S. PATENT DOCUMENTS

| | | | |
|---|---|---|---|
| 4,683,142 | 7/1987 | Zimmerman et al. | 427/2.24 |
| 4,962,891 * | 10/1990 | Layden | 239/597 |
| 5,111,976 | 5/1992 | Ban | 222/485 |
| 5,171,367 | 12/1992 | Fitch, Jr. | 118/25 |
| 5,368,563 | 11/1994 | Lonneman et al. | 604/82 |
| 5,464,471 | 11/1995 | Whalen et al. | 106/124.4 |

* cited by examiner

PROCESS FOR THE PRODUCTION OF A MATERIAL FOR SEALING AND HEALING WOUNDS

This is a continuation-in-part of Ser. No. 08/437,232, filed May 8, 1995, pending, which is a continuation-in-part of Ser. No. 08/220,877, now abandoned, filed Mar. 31, 1994.

BACKGROUND OF THE INVENTION

The invention relates to a process for the production of a material for sealing and/or healing wounds which comprises the even application of a liquid composition to a suitable carrier.

A material for sealing and healing wounds which comprises a collagen carrier, coated with a fibrinogen component, a thrombin component and possible additional components is known from U.S. Pat. No. 4,453,939.

To prepare a material of this kind, a fibrinogen component, a thrombin component and possible additives are suspended in an organic solvent, e.g. ethanol, and subsequently applied to a suitable carrier, e.g. by means of spraying.

In spraying such a suspension containing a fibrinogen component and a thrombin component on the carrier, several problems arise, because the suspension to be applied is difficult to handle. For example, the nozzles usually used for these purposes clog immediately. Air atomizing nozzles permit the use of a larger diameter, but even in this case, only nozzles with the largest diameter available allow working with a sufficient lack of trouble. However, these nozzles show a fatal disadvantage. The indistinct definition of the exiting stream does not result in an application of an even layer of the suspension, but creates a trapezoidal coating profile on the carrier. This leads to considerable losses of valuable and expensive suspension and of carrier material at the edges.

A device for applying a liquid film to a fabric web according to the pouring-out principle is known from EP-A 472 050. By means of individual partitions for liquid which are located directly next to one another, this device achieves a forced distribution of the liquid from a feed opening to a number of outflow openings. The liquid is distributed in the form of a family tree, i.e step by step from one opening to two, four, eight, sixteen, etc. outflow openings. Such a device is not suitable for an even distribution of a suspension containing fibrinogen and thrombin components, as the several divisions of the liquid stream cause conglutination and clogging of the partitions by the suspension. Furthermore, such a conglutination and clogging occurs to a greater extent than when nozzles are used.

SUMMARY OF THE INVENTION

The problem solved by the present invention is therefore to substantially reduce or preferably prevent the disadvantages of the previously known methods. Especially, the present inventors have focused on reducing and/or avoiding the disadvantages of the known methods with respect to i) the considerable loss of very expensive material and to ii) separation of the components contained in the suspension during application of the suspension on the carrier; the latter disadvantage has also shown to be dependent on variations of the suspension (e.g. with respect to temperature, viscosity, composition etc.). All these problems have been realized with the known methods.

An object of the present invention is therefore a process for the production of a material for sealing and/or healing wounds, comprising:

i) filling a liquid composition into a container having two or more plates, at least two of the plates being perforated with one or more flow-through holes and at least one of the perforated plates being movable relative to another of the perforated plates, ii) transporting a suitable carrier below the container in a transport direction, and iii) continuously moving the perforated plates relative to each other so as to allow the liquid composition to drip on to the carrier being transported below the container, whereby the liquid composition is substantially evenly applied to the carrier.

Although the process according to the invention in particular is useful when a suspension is to be applied on a carrier, the novel process is also suitable for the application of any liquid composition. The process involves the use of a device which enables adjustment of how and how fast a liquid composition is applied on a carrier, and such adjustment measures enable a more general applicability than just for liquid compositions in the form of a suspension. In the present context the term "liquid composition" therefore covers suspensions as well as solutions, mixtures, dispersions, emulsions, and lotions.

A novel device is also an object of the present invention, namely a device for even application of a liquid composition to a carrier for the production of a material for sealing and healing wounds. The device comprises a container into which the liquid composition is filled and which has a base frame and two perforated plates forming a bottom of the container, the two perforated plates including an upper plate and a lower plate, the plates being movable relative to each other so as to allow a continuous back and forth movement of the upper plate, whereby the liquid composition is evenly applied to the carrier, the carrier being transported below the device in a transport direction.

In a more specific embodiment, the invention relates to a process for the production of a material for sealing and/or healing wounds, comprising:

i) filling a suspension into an elongated container, the elongated container having a base frame and two perforated plates forming a bottom of the elongated container, the two perforated plates including an upper plate and a lower plate, the upper plate being movable relative to the lower plate, ii) transporting a carrier below the elongated container in a transport direction, and iii) continuously moving the upper plate back and forth so as to allow the suspension to drip on to the carrier being transported below the elongated container, whereby the suspension is substantially evenly applied to the carrier.

In still another embodiment the invention relates to a process for the production of a material for sealing and healing wounds which comprises the even application of a suspension to a suitable carrier, characterized in that the elongated container, into which the suspension is filled, is provided with a base which allows the suspension to drip on the carrier which is transported underneath the container. The drops are guided by e.g., a sharp cannula or a needle.

The invention also relates to a method for healing and/or sealing wounds comprising applying on the wound a material prepared as in the process of the present invention.

Furthermore, the invention relates to a method for stopping oozing blood from wounds comprising applying on the wound a material prepared as claimed in the process of the present invention.

It is important to note that a process according to the present invention is not limited to the preparation of a wound healing and/or sealing material. The process is generally applicable and especially useful for the preparation of biocompatible material for use in, e.g., surgery or minimally invasive surgery and for use in other circumstances where healing and/or sealing of a wound is required. The composition contained on a biocompatible carrier is effective as, e.g., healing and/or sealing wounds but the invention is not limited to a process for the preparation of such a material within the scope of the invention is also a process for the preparation of biocompatible material wherein the composition applied on the carrier also may contain other drug substance(s) useful in therapy (e.g. anti-inflammatory agents, antiviral agents, anti-infective agents, growth factors, etc.) optionally in combination with an agent for healing and/or sealing wounds.

Suitable carrier materials for use in a process according to the invention are biocompatible materials. The carrier (i.e. the carrier material) may be bio-degradable or self-dissolving materials like collagen, gelatin, oxidized cellulose, polyglycolic acid, polylactic acid, polyhydroxybutyric acid in non-woven and woven form or non-degradable materials like polyethylene, polypropylene, polyamide, polyester, polypropyxypolyamide, polyurethane in non-woven and woven form. Among the degradable materials, collagen is the preferred material. Foam is the most preferred form of polyurethane.

A material for sealing and/or healing wounds based on a biodegradable carrier material are produced to stay (remain) in the wound and to be degraded within the body. Thus, such a material is not removed by physical means, but is enzymatically degraded in the body.

A material for sealing and/or healing wounds based on a non-degradable carrier material is in particular produced to stop oozing blood, and the carrier material can be removed after a short time (preferably within the course of an operation) optionally leaving at least a part of the active wound healing and/or sealing agents on the surface of the wound. Preferably, a significant or substantial amount of the active wound healing and/or sealing agents is left on the surface of the wound when the carrier material is removed.

Preferred active wound healing and/or sealing agents are fibrinogen, fibrinogen components, thrombin and/or thrombin components and mixtures thereof. Optionally, other drug substances such as, e.g., aprotinin can be added (aprotinin acts as a protease inhibitor). Other relevant additives are calcium ions, protease inhibitors or heparin antagonists.

The most preferred liquid composition to be filled into a container of the device according to the present invention is a suspension comprising a fibrinogen component, a thrombin component, and optional additives such as aprotinin (which acts as protease inhibitor), calcium ions or heparin antagonists in alcohol such as ethanol, n- or i-propanol or other organic solvents. This suspension is useful for the production of a material for sealing and/or healing wounds and for other medical uses. For this reason, the device, especially the perforated plates, must be constructed of a material which is abrasion-resistant and chemically inert to the components of the suspension. Suitable materials would be for example steel such as, e.g., high grade steel, titanium, stone (e.g. marble, lime stone), ceramics, carbon, carbonaceous material, and plastics including self-degrading plastics. The lateral boundary walls in a specific embodiment according to the invention can also be constructed of glass or plexiglass, which in transparent form makes it possible to easily observe the suspension in the container. An observation and control of the suspension in the container is desirable in order to control make sure that the suspension does not separate, sediment and/or forms a cream during the application of the suspension on the carrier. If such a separation occurs, the process can easily be stopped and/or adjusted. Furthermore, such an inspection also makes it possible to control any clogging and/or conglutination of the suspension.

One embodiment of said container is provided with a rectangular perforated plate (base plate (2)) which is surrounded by the base frame (1) and upon which lateral boundary walls rest. A second perforated plate is mounted directly above the perforated base plate (2) and this plate can be moved back and forth inside the container as a movable perforated plate (3).

BRIEF DESCRIPTION OF THE DRAWINGS

Further features and advantages of the present invention will become clear from the following description thereof, taken in consideration of the drawing figures, in which:

FIGS. 5A, 5B 5C are different views of an embodiment for use in a process of the invention; a container is elongated and constructed as a tube or a semi-tube provided with holes at its bottom and into which a movable perforated tube or semi-tube or partial tube is fitted. Alternatively, the container is movable and/or both the container and the tube or semi-tube are movable.

FIG. 6 illustrates a further embodiment of the invention wherein a lower plate is stationary and an upper plate is movable. The container has a polygonal shape (in this case a rectangular shape).

FIG. 7 is a top view of perforated plates; the lower plate is indicated by a dotted line in alignment with the upper plate, which is indicated by a continuous line. The upper plate can be moved in any direction in the plane of the paper to get both plates out of alignment. For construction reasons, back and forth movement in either the transport direction or at a transverse angle such as a right angle to the transport direction are preferred.

FIG. 8 illustrates the distance between neighbouring holes in a transverse direction in relation to the transport direction.

FIG. 9 illustrates various back and forth movements of the plates in an elongated container with respect to the transport direction.

FIG. 10 illustrates a stationary level of a liquid composition.

DETAILED DESCRIPTION OF THE PREFERRED EMBODIMENTS

With a process according to the present invention, an even application of a suspension to a collagen carrier results in the production of a material for sealing and healing wounds. A container (preferably in the form of an elongated container) into which the liquid composition (e.g. a suspension) is filled is provided with a base frame 1 and a set of two perforated plates 2, 3. More than two plates may be present such as, e.g., 3, 4, 5 or 6 plates. However, at least two plates are perforated and in a preferred embodiment the two perforated plates form the bottom of the container. All plates may be movable, and especially the perforated plates are movable relative to each other, i.e. either only one of the perforated plate is movable or both of the plates are movable. In FIG. 1 the two perforated plates are situated on top on each other. The plate 3 is the upper plate, and is movable. However, plate 2 could as well be movable. During operation the plates are continuously moved relative to each other. They (or only one of the plates such as, e.g., the upper or the lower plate) are continuously moved back and forth e.g. substantially parallel or transverse to the transport direction such as, e.g., substantially perpendicular or at a right angle to the direction of transport of the carrier. In a presently preferred embodiment, the carrier is a collagen carrier. This allows the liquid composition to drip onto the carrier that is transported below the container.

The plate 2 is a base plate, and is a rectangular perforated plate that is surrounded by a base frame 1. However, the base plate need not be of a rectangular shape. Any shape is possible, i.e. any polygonal shape or a circular or tube-like shape. A lateral boundary wall of the base frame 1 rests upon the base plate 2. The movable perforated plate 3 is mounted directly above the perforated base plate 2, and it can be moved back and forth inside the container. In an alternative embodiment, the perforated plate 2 is stationary while the container is movable.

Figure 5:
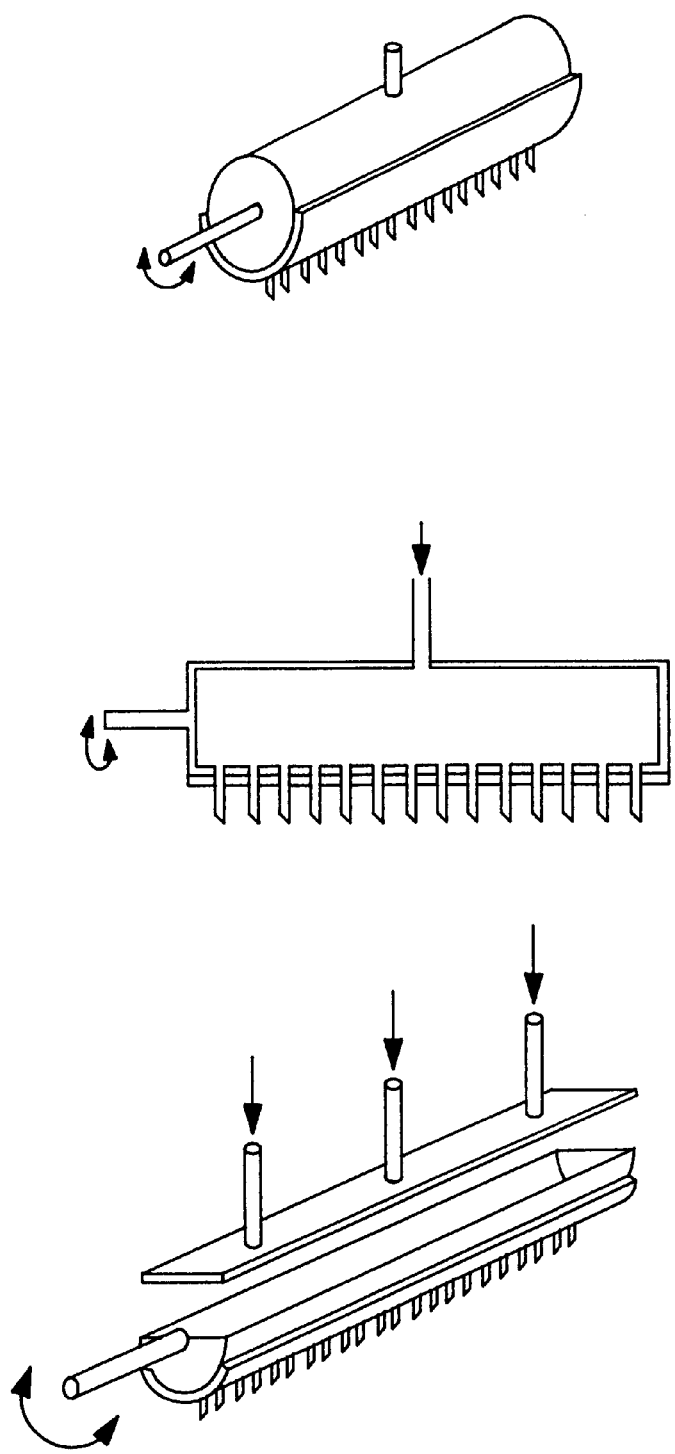

The liquid composition such as, e.g., a suspension to be filled into the container normally contains at least one substance which is an effective wound healing and/or sealing agent. Active agents are, e.g. a fibrinogen component, a thrombin component and, furthermore, the liquid composition may contain other additives such as aprotinin (which acts as a protease inhibitor), calcium ions or heparin antagonists. Suitable solvents/dispersion media are alcohols such as ethanol, n- or i-propanol or n- or i-butanol. Such a liquid composition is normally presented as a suspension which is used for the production of material for sealing and/or healing wounds and for other medical uses. For this reason, the device, and especially the perforated plates, must be constructed of a material that is abrasion resistant and chemically inert to the components of the suspension.

Suitable materials include, for example, steel such as high grade steel, titanium, stone including marble and lime stone, ceramics, carbon, carbonaceous material and plastic. The lateral boundary walls can also be constructed of glass or plexiglass, which in transparent form makes it possible to easily observe the suspension inside the container.

Both perforated plates are provided with at least one flow-through hole. In general, one or more rows of flow-through holes are present on the plates, whereby the holes in the rows are arranged at a certain distance such as equal distances. Preferably the plates are provided with several equidistant rows of holes.

When the liquid composition is a suspension, the diameter of the flow through holes chosen must be large enough to prevent the suspension from clogging the holes.

The ratio of the flow-through holes' diameter to that of the largest particle in the suspension amounts to approximately 5:1 to 50:1, preferably 7.5:1 to 40:1 and most preferably 10:1 to 30:1.

The largest particles in the suspension measure approximately 0.1 mm to 0.2 mm in diameter.

The centers of the flow-through holes are preferably located at a distance of approximately 2 to 8 mm, especially preferably at a distance of 3–4.5 mm at a right angle to the transport direction of the carrier.

Depending on the number of rows, the distance between the neighbouring holes in a row can measure up to 16 mm and more.

With respect to the distance between neighbouring holes in different rows, this distance is illustrated in FIG. 8 and is normally from about 2 to about 8 mm such as, e.g. from about 3.5 mm to about 4 mm.

In applying the liquid composition in the form of a suspension to a suitable carrier, the previously homogenized suspension is pumped into the container at a constant speed with the movable perforated plates lying on top of each other, in the beginning in such a way as to close the flow-through holes. The sealing should be as efficient as possible and can optionally be assisted by bearing weights.

As soon as the suspension in the container has reached the stationary level corresponding to the given pumping speed, the coating apparatus is put into operation. [The stationary level is illustrated in FIG. 10; a stationary level of a liquid can be demonstrated by pouring a stream of water at a constant rate into a funnel. The stationary level is reached when the flow rate into the funnel is the same as the flow rate leaving the funnel. Higher flow rates result in higher stationary levels. More narrow outlets of the funnel—corresponding to a higher deflection distance—also result in higher stationary levels.] The movable perforated plate is caused to move back and forth over the stationary perforated plate. The two sets of rows become congruent at a certain position (preferably in the middle between the two stationary points at which the movable perforated plate changes direction) and the suspension can drip onto the carrier, which is passed under the coating apparatus.

The level of the suspension in the coating apparatus remains constant (=stationary level) during this process provided that additional suspension is continuously pumped in.

Varying deflectional distances of the movable perforated plate allow a wide range for setting the ratio of the intervals of closure and opening. This makes it possible to choose hole diameters of a size where no complications arise and, at the same time, to regulate the drop rate.

It can be achieved that the points where the drops hit the surface of the carrier form the corners of equilateral triangles thus corresponding to layers of sheets packed as tightly as possible. This requires a certain arrangement of holes in the perforated plates and a certain frequency of oscillation at a given speed of transportation of the carrier. This frequency, or frequencies higher than this, are preferred.

The perforated plate of the described embodiment of the elongated container preferably moves substantially parallel or substantially perpendicular, i.e. at a right angle, to the transport direction of the carrier.

The relative movement such as the relative lateral movement, of the perforated plates (e.g. a back and forth movement of the movable perforated plate), simultaneously ensures that a suspension remains homogeneous, so that an even distribution of the components is achieved on the carrier. Mixing can be assisted optionally by means of additional arrangements on the movable perforated plate or by a mixer.

Another embodiment of the container into which the suspension is filled can be constructed as a tube or semi-tube provided with holes into which a movable tube or semi-tube perforated in the same pattern is mounted. Moving the inner tube causes periodical opening and closing of the holes, thus achieving the desired effect (FIG. 5).

Figure 6:
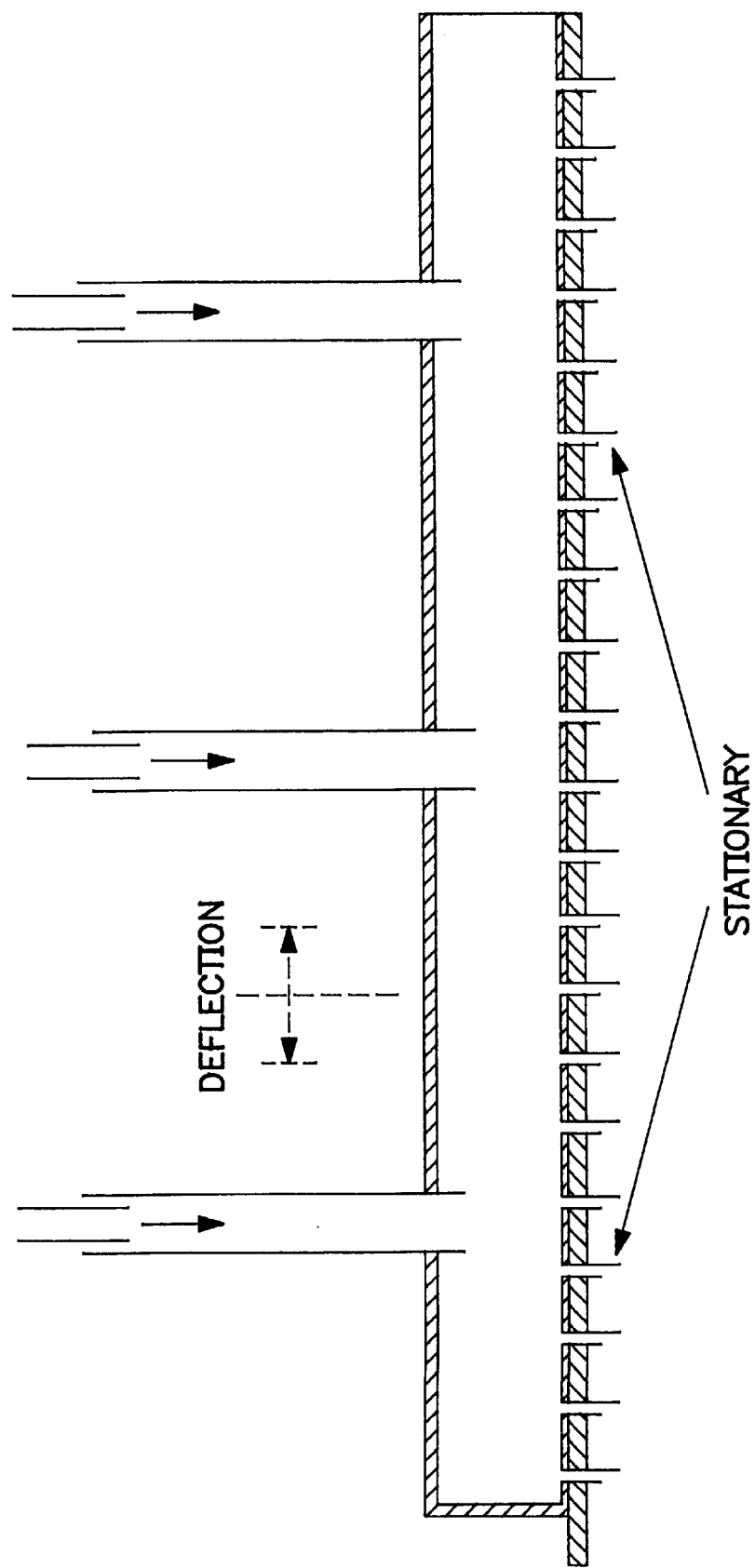
Figure 7:
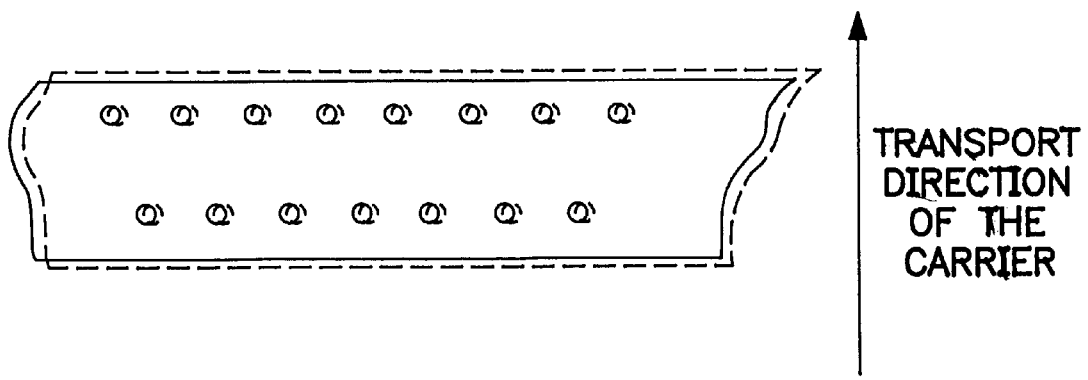
Figure 8:
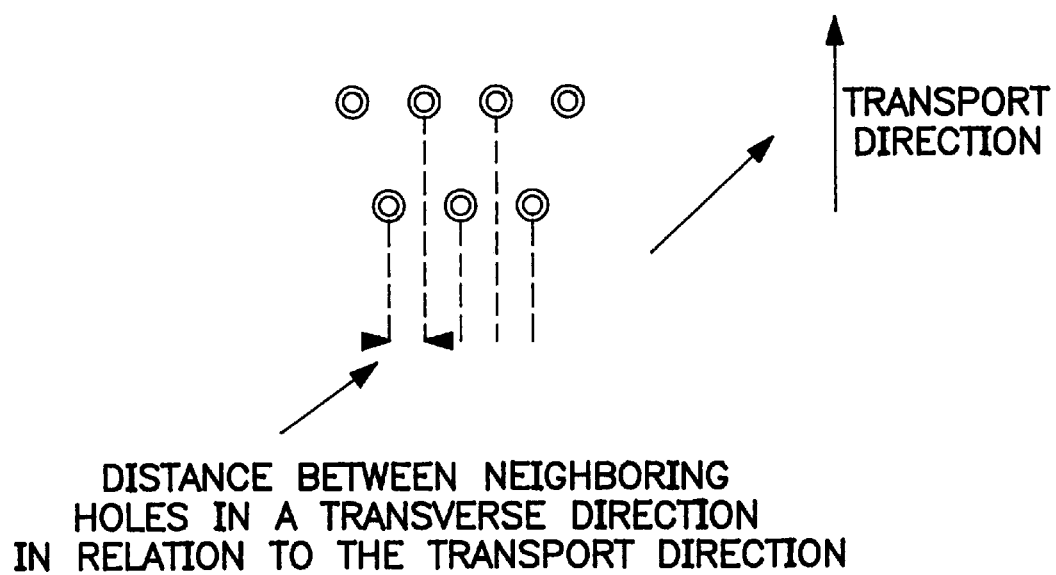
Figure 9:
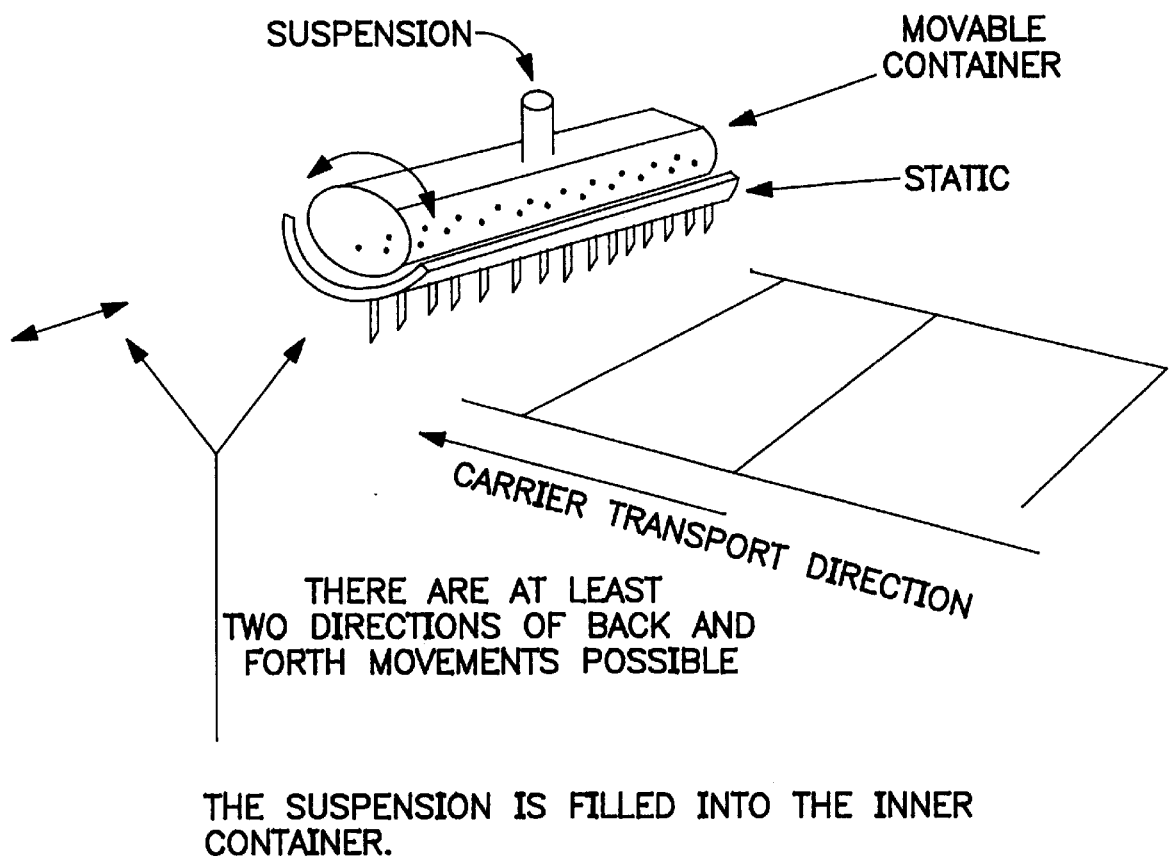
Figure 10:
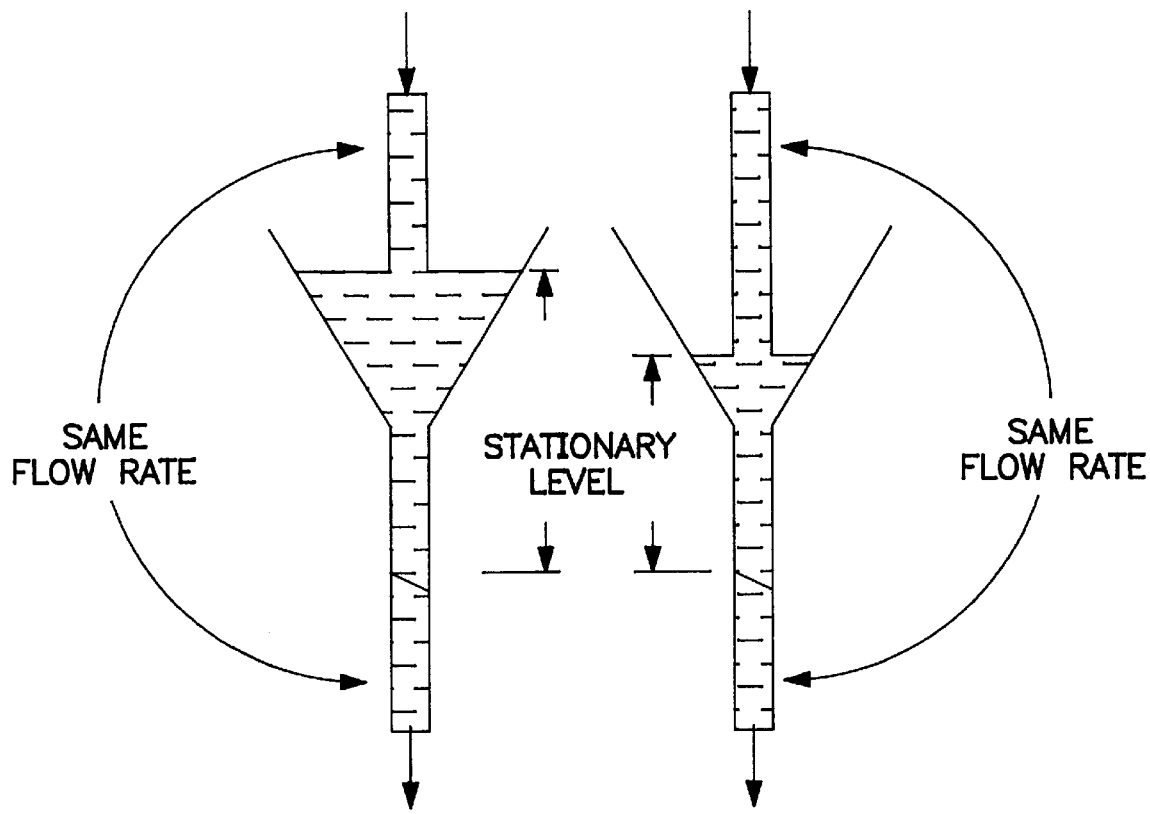

Another embodiment of the container into which the suspension is filled can be constructed as a polygonal, such as, e.g., a rectangular, vessel with a perforated bottom. This container is moved back and forth on top of a plate perforated in the same pattern, thus achieving the above described effect (FIG. 6).

With the process according to the invention, applying an exactly defined breadth of the suspension is possible without loss of suspension or carrier material at the edges.

The profile of the coating achieved after evaporation of the suspension medium is not trapezoidal (as it is when using known spraying techniques), but rectangular.

A comparative test, in which the loss at the edge resulting when using the previously known spraying technique, in which an air atomizing nozzle is used, is compared to the loss resulting with the process according to the invention, shows that more than five times more suspension is lost with the air atomizing nozzle than with the process according to the invention.

A relatively small batch was used in this test. The ratio increases correspondingly as the batch size increases. A loss of suspension during application with the process according to the invention occurs only with the residual volume of suspension remaining in the container after pumping ceases.

Other interesting embodiments are claimed in the claims and are seen in the figures.

As mentioned above, the invention also relates to a device suitable for an even application of a liquid composition on a suitable carrier and it further relates to a method for healing and/or sealing wounds and for stopping oozing blood. It is understood that all the particulars described above with respect to the process also apply mutatis mutandis to all the other aspects of the invention.

EXAMPLE 1

Figure 1:
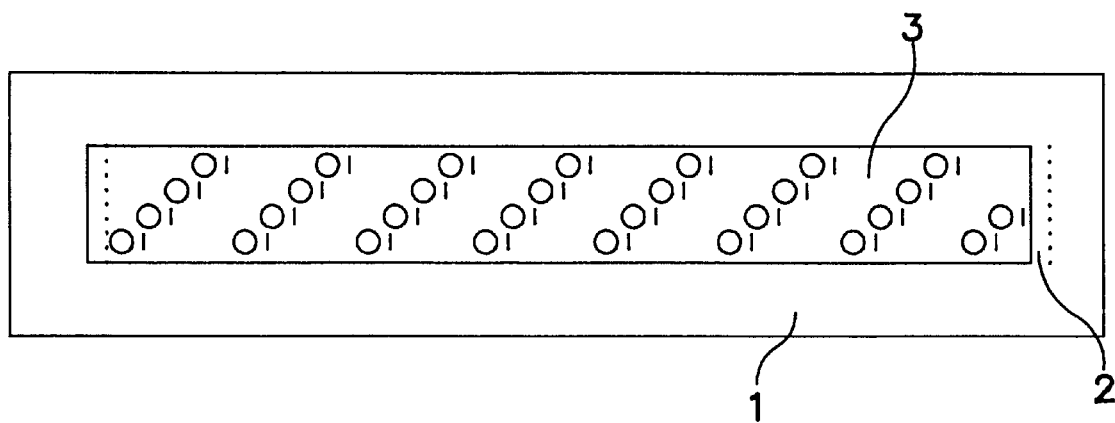
FIG. 1 is a plan view of an elongated container for use with the process according to the present invention.
Figure 2:
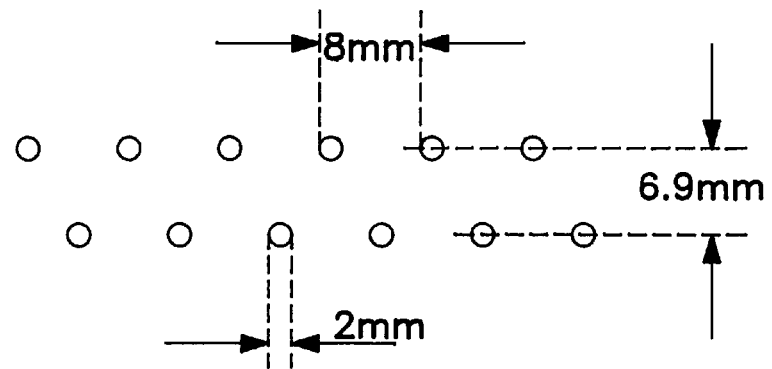
FIG. 2 is a schematic illustration of one example of flow-through holes for the container of FIG. 1.

Into a container provided with a perforated base plate and a movable perforated plate on top of it, with the following dimensions:
Breadth: 450 mm
Depth: 12 mm
Number of rows of holes: 2
Diameter of flow-through holes: 2 mm
Distance between the centres of the two flow through holes located in one row: 8 mm
Distance between the rows of holes: 6.9 mm
(The arrangement of the flow-through holes is shown in FIG. 2), in which the perforated plates were closed, a suspension of 55 mg/ml of fibrinogen 20 lU/ml of thrombin and 0.71 Ph. Eur. U/ml of aprotinin in ethanol is pumped at a speed of 450 ml/min. When the stationary level of the liquid of 50 mm is reached, the movable perforated plate is put into motion at 200 cycles/min, whereby the deflection measures 6 mm in both directions.

A breadth of 450 mm of the suspension is then dripped onto a collagen carrier measuring 5 mm in height which carrier is being transported underneath the container at a speed of 1 m/min and at a right angle to the movement of the movable perforated plate. After evaporation of the suspension liquid the collagen carrier is coated with approximately 5.5 mg/cm$^2$ of fibrinogen, 2 IU/cm$^2$ of thrombin and 0.071 Ph.Eur.U/cm$^2$ of aprotinin.

The loss at the edge is less than 1%.

Figure 3:
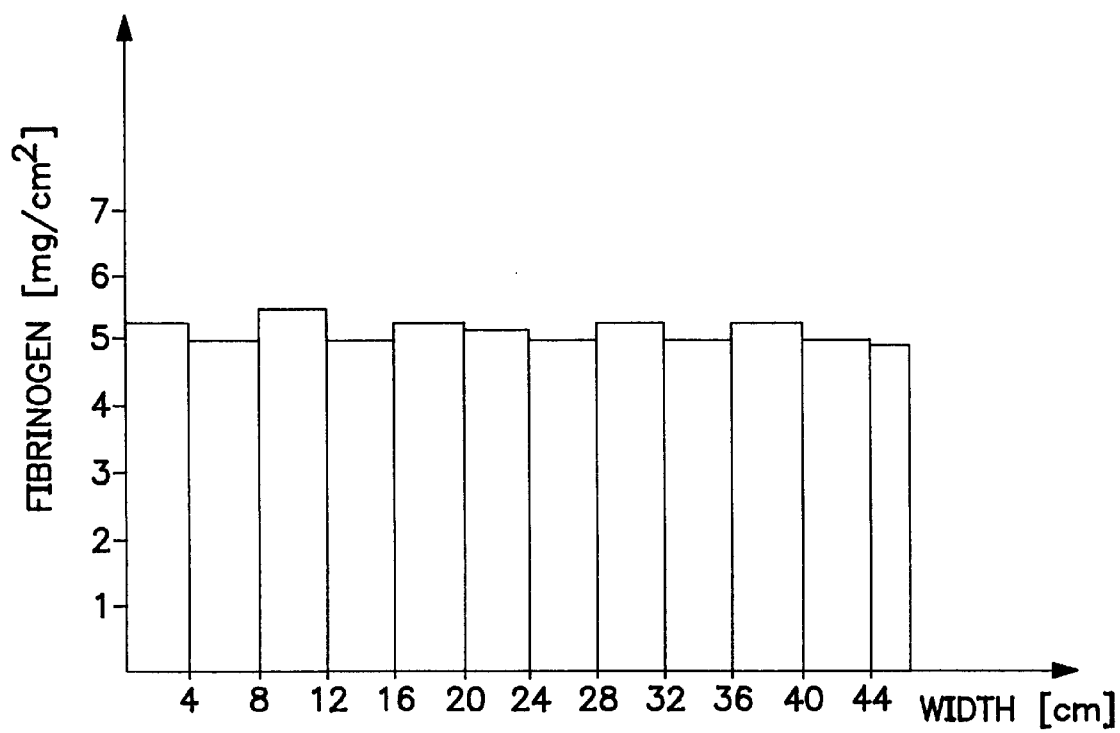
FIG. 3 is a graph illustrating a profile of the amount of coating per square centimeter viewed at a right angle to the direction of transport when a coating is applied according to a process of the present invention.

The profile of the coating under these conditions at a right angle to the direction of transport is shown in FIG. 3.

COMPARATIVE EXAMPLE

Figure 4:
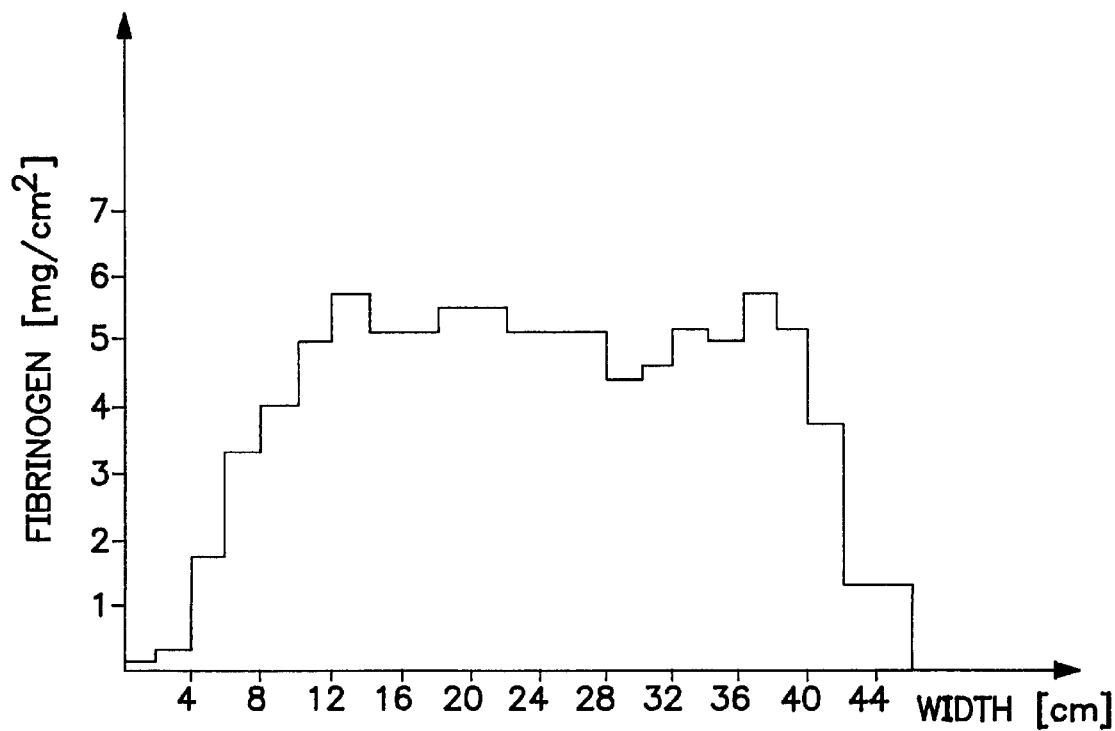
FIG. 4 is a profile similar to FIG. 3, but of the best result achieved in numerous tests with various atomized air nozzles for the application of a suspension to a collagen carrier.

A breadth of 450 mm of a suspension with the same composition is again applied to a collagen carrier which is transported in the same manner as in the above example. FIG. 4 shows the best result achieved in numerous tests with various air atomizing nozzles.

In this example, an air atomizing nozzle combination from Spraying Systems Inc., which features a turnaround surface, was used. The best sample was chosen from numerous examples of the same model.

The profile of the coating of fibrinogen at a right angle obtained by spraying to the direction of transport is shown in FIG. 4. Even under these conditions, the loss of suspension falling from both sides still amounts to approximately 20%.

EXAMPLE 2

A container having two half-tubes, a smaller one which is fitting into a larger one as shown in FIG. 5 with the following dimensions, is used:

| | |
|---|---|
| Breadth | 600 mm |
| Inner diameter of the inner tube | 25 mm |
| Both tubes have the same pattern of flow through holes: | |
| Number of rows of holes | 2 |
| Diameter of flow through holes | 3 mm |
| Distance between the centres of two flow through holes located in one row | 7 mm |
| Distance between the row of holes | 16 mm |

A suspension in isopropanol of
60 mg/ml fibrinogen, and
22 IU/ml thrombin
is pumped into the inner tube at a rate of 500 ml/min while the flow through holes are out of alignment. When the stationary level is reached, the inner tube is continuously turned back and forth by an angle of 90° with 135 cycles/min while a carrier of polyglycolic acid is transported underneath with 0.93 m/min.

EXAMPLE 3

A rectangular container with a perforated base is placed in a guided movable fashion on a plate perforated in the same pattern.

In principle the guided oscillating movement may be in all lateral directions. In this example, it shall be in the direction of the longitudinal axis.

| | |
|---|---|
| Dimensions: | |
| Breadth | 250 mm |
| Depth | 25 mm |
| Number of rows of holes | 4 |
| Diameter of flow through holes | 2.5 mm |
| Distance between the centre of the flow through holes in one row | 12 mm |
| Distance between the rows of holes | 5 mm |

A suspension in acetone of
50 mg/ml fibrinogen, and
18 IU/ml thrombin
is pumped into the container at a rate of 400 ml/min while the flow through holes are out of alignment. When the stationary level is reached, the container is continuously moved back and forth with 240 cycles/min at a deflection of 8 mm in both directions while a carrier of polyethylene is transported underneath with a speed of 1.45 m/min.

We claim:

1. A process for the production of a material for sealing and/or healing wounds, comprising:
   i) filling a liquid composition into a container having two or more plates, at least two of said plates being perforated with one or more flow-through holes and at least one of said perforated plates being movable relative to another of said perforated plates,
   ii) transporting a carrier below the container in a transport direction, and
   iii) continuously moving the perforated plates relative to each other so as to allow the liquid composition to drip on to the carrier being transported below the container, whereby the liquid composition is substantially evenly applied to the carrier.

2. The process of claim 1, wherein the container has two perforated plates.

3. The process of claim 1, wherein the container is an elongated container.

4. The process of claim 1, wherein the liquid composition is in the form of a suspension.

5. The process of claim 1, wherein the continuous movement of the perforated plates is a movement of the plates back and forth relative to each other.

6. The process of claim 1, wherein the container has a base frame and two of said perforated plates form a bottom of the container.

7. The process of claim 1, wherein the at least two perforated plates include an upper and a lower plate and the upper plate is movable relative to the lower plate.

8. The process of claim 1, wherein the at least two perforated plates include an upper and a lower plate and the lower plate is movable relative to the upper plate.

9. The process of claim 1, wherein the at least two perforated plates are mounted on top of each other and perforated in substantially the same pattern, the plates being laterally movable relative to each other so as to allow the container to close and open.

10. The process of claim 1, wherein said transporting and said continuously moving the perforated plates relative to each other occur simultaneously.

11. The process of claim 1, wherein the perforated plates are moved back and forth relative to each other.

12. The process of claim 1, wherein said continuously moving the perforated plates comprises movement in a direction that is substantially parallel to the transport direction of the carrier.

13. The process of claim 1, wherein said continuously moving the perforated plates comprises movement in a direction that is transverse to the transport direction of the carrier.

14. The process of claim 13, wherein said transverse direction is substantially perpendicular to the transport direction of the carrier.

15. The process of claim 7, wherein the upper and the lower perforated plates have an aligned position so that at least one of the flow-through holes on the upper plate is directly above at least one of the flow-through holes on the lower plate.

16. The process of claim 7, wherein the perforation pattern of flow-through holes on the upper and lower perforated plates is substantially the same and the plates have an aligned position in which the flow-through holes on the upper plate correspond with the flow-through holes on the lower plate.

17. The process of claim 7, wherein a deflection distance of the upper and lower perforated plates is set from a position of alignment of the upper and lower perforated plates so that said continuously moving the perforated plates relative to each other regulates the rate at which the liquid composition drips on the carrier.

18. The process of claim 1, wherein the at least two perforated plates are made from a material selected from the group consisting of steel, titanium, stone, ceramics, carbon, carbonaceous material, and plastic.

19. The process of claim 1, wherein at least part of the container is made of a transparent material.

20. The process of claim 6, wherein the base frame has lateral boundary walls that are made of a transparent material.

21. The process of claim 1, wherein each of the perforated plates comprises at least one row of flow-through holes arranged at equal distances with respect to each other.

22. The process of claim 1, wherein the liquid composition comprises particles therein and wherein the ratio of the diameter of flow-through holes in said at least two perforated plates to the largest of the particles is approximately from 5:1 to 50:1.

23. The process of claim 22, wherein the ratio is approximately 7.5:1 to 40:1.

24. The process of claim 23, wherein the ratio is approximately 10:1 to 30:1.

25. The process of claim 1, wherein the container is formed as a rectangular elongated container with a perforated bottom as one of the at least two perforated plates and a base frame within the container which holds the movable perforated plate.

26. The process of claim 1, wherein the container into which the liquid composition is filled is constructed as a tube or a partial tube provided with holes at its bottom and into which a movable perforated tube or partial tube is fitted.

27. The process of claim 1, wherein the container into which the liquid composition is filled is constructed as a tube or a partial tube provided with holes at its bottom which is fitted into a movable perforated tube or partial tube.

28. The process of claim 1, wherein said filling comprises pumping the liquid composition into the container at a set constant speed with perforations in the two perforated plates being out of alignment so that the container is closed, and wherein said transporting and said continuously moving start when the liquid composition in the container has reached a level at which, for a given pumping speed, the level will remain stationary during said transporting and said continuously moving.

29. The process of claim 28, wherein the level of the liquid composition is maintained constant during said steps of transporting and continuously moving.

30. The process of claim 1, wherein the liquid composition is a suspension comprising a fibrinogen component and a thrombin component whereby a single layer containing the fibrinogen component and the thrombin component is formed on the carrier during said continuously moving.

31. The process according to claim 1, wherein the liquid composition comprises aprotinin.

32. The process of claim 1, wherein the liquid composition comprises an organic solvent.

33. The process of claim 31, wherein the liquid composition further comprises an alcohol.

34. The process of claim 1, wherein the two perforated plates comprise respective rows of evenly spaced flow-through holes that are alignable and misalignable with each other during said continuously moving.

35. The process of claim 1, further comprising mixing the liquid composition during said continuously moving.

36. The process of claim 1, wherein said carrier is a biocompatible material.

37. The process of claim 1, wherein said carrier is a bio-degradable material.

38. The process of claim 1, wherein said carrier is non-biodegradable.

39. The process of claim 37, wherein said carrier comprises a material selected from the group consisting of collagen, gelatin, oxidized cellulose, polyglycolic acid, polylactic acid, and polyhydroxybutyric acid.

40. The process of claim 38, wherein said carrier comprises a material selected from the group consisting of polyethylene, polypropylene, polyamide, polyester, polypropyxypolyamide, and polyurethane.

41. The process of claim 39, wherein said carrier is a collagen carrier.

42. The process of claim 40, wherein said carrier is a polyurethane carrier and the polyurethane is in the form of a foam.

43. A process for the production of a material for sealing and/or healing wounds, comprising:
   i) filling a suspension into an elongated container, the elongated container having a base frame and two perforated plates forming a bottom of the elongated container, the two perforated plates including an upper plate and a lower plate, the upper plate being movable relative to the lower plate,
   ii) transporting a carrier below the elongated container in a transport direction, and
   iii) continuously moving the upper plate back and forth so as to allow the suspension to drip on to the carrier being transported below the elongated container,
   whereby the suspension is substantially evenly applied to the carrier.

44. The process of claim 43, wherein said continuously moving the upper plate back and forth is in a direction that is substantially parallel to the transport direction of the carrier.

45. The process of claim 43, wherein said continuously moving the upper plate back and forth is in a direction that is transverse to the transport direction of the carrier.

46. The process of claim 45, wherein said transverse direction is substantially perpendicular to the transport direction of the carrier.

47. The process of any of claims 43, wherein said transporting and said continuously moving the upper plate back and forth occur simultaneously.

48. The process of claim 43, wherein said continuously moving further comprises regulating the flow rate of the suspension by setting a deflection distance of the upper plate.

49. The process of claim 43, wherein the two perforated plates are made from a material selected from the group consisting of steel, titanium, stone, ceramics, carbon, carbonaceous material, and plastic.

50. The process of claim 43, wherein the elongated container is in part made of a transparent material.

51. The process of claim 43, wherein the base frame has lateral boundary walls that are made of a transparent material.

52. The process of claim 43, wherein each of the perforated plates comprises at least one row of holes arranged at equal distances with respect to each other.

53. The process of claim 52, wherein the suspension comprises particles therein and wherein the ratio of the diameter of flow-through holes in said two perforated plates to the largest of the particles is approximately from 5:1 to 50:1.

54. The process of claim 53, wherein the ratio is approximately 7.5:1 to 40:1.

55. The process of claim 54, wherein the ratio is approximately 10:1 to 30:1.

56. The process of claim 43, wherein the container is formed as a rectangular elongated container with the base frame of the container holding the perforated movable upper plate.

57. The process of claim 43, wherein the container into which the suspension is filled is constructed as a tube or a partial tube provided with holes at its bottom and into which a movable perforated tube or partial tube is fitted.

58. The process of claim 43, wherein the container into which the suspension is filled is constructed as a tube or a semi-tube provided with holes at its bottom which is fitted into a movable perforated tube or semi-tube.

59. The process of claim 43, wherein said filling comprises pumping the liquid composition into the container at a set constant speed with perforations in the two perforated plates being out of alignment so that the container is closed, and wherein said transporting and said continuously moving start when the liquid composition in the container has reached a level at which, for a given pumping speed, the level will remain stationary during said transporting and said continuously moving.

60. The process of claim 59, wherein the level of suspension is maintained constant during said transporting and said continuously moving.

61. The process of claim 43, wherein the suspension comprises a fibrinogen component and a thrombin component, whereby a single layer containing the fibrinogen component and the thrombin component is formed on the suspension carrier during said continuously moving.

62. The process according to claim 43, wherein the suspension comprises aprotinin.

63. The process of claim 43, wherein the suspension comprises an organic solvent.

64. The process of claim 61, wherein the suspension is in alcohol.

65. The process of claim 43, wherein the two perforated plates comprise respective rows of evenly spaced flow-through holes that are alignable and misalignable with each other in the two perforated plates during said continuously moving.

66. The process of claim 65, further comprising mixing the suspension during said continuously moving.

67. The process of claim 43, wherein said carrier is a biocompatible material.

68. The process of claim 43, wherein said carrier is a biodegradable material.

69. The process of claim 43, wherein said carrier is non-biodegradable.

70. The process of claim 68, wherein said carrier is selected from the group consisting of collagen, gelatin, oxidized cellulose, polyglycolic acid, polylactic acid, and polyhydroxybutyric acid.

71. The process of claim 69, wherein said carrier is selected from the group consisting of polyethylene, polypropylene, polyamide, polyester, polypropyxypolyamide, and polyurethane.

72. The process of claim 70, wherein said carrier is a collagen carrier.

73. The process of claim 71, wherein said carrier is a polyurethane carrier and the polyurethane is in the form of a foam.

74. The process of claim 32, wherein the organic solvent comprises an alcohol.

75. The process of claim 63, wherein the suspension is in alcohol.

76. The process of claim 43, wherein the two perforated plates are made from a material selected from the group consisting of marble and limestone.

* * * * *